United States Patent [19]
NessAiver

[11] Patent Number: 5,348,011
[45] Date of Patent: Sep. 20, 1994

[54] SHARED EXCITATION PHASE ENCODE GROUPING FOR IMPROVED THROUGHPUT CARDIAC GATED MRI CINE IMAGING

[75] Inventor: Moriel S. NessAiver, Cleveland Heights, Ohio

[73] Assignee: Picker International, Inc., Highland Hts., Ohio

[21] Appl. No.: 982,569

[22] Filed: Nov. 27, 1992

Related U.S. Application Data

[63] Continuation-in-part of Ser. No. 874,807, Apr. 28, 1992, and Ser. No. 859,153, Mar. 27, 1992, which is a continuation-in-part of Ser. No. 791,855, Nov. 14, 1991, Pat. No. 5,273,040.

[51] Int. Cl.$^5$ .............................................. A61B 5/055
[52] U.S. Cl. .................................. 128/653.2; 128/696; 128/708
[58] Field of Search ............... 128/653.2, 653.3, 653.5, 128/696, 708; 324/306, 309

[56] References Cited

U.S. PATENT DOCUMENTS

| | | | |
|---|---|---|---|
| 4,683,431 | 7/1987 | Pattany et al. | 324/306 |
| 4,689,560 | 8/1987 | Nayler et al. | 324/306 |
| 4,710,717 | 12/1987 | Pelc et al. | 128/653.2 |
| 4,724,386 | 2/1988 | Haacke et al. | 324/306 |
| 4,739,766 | 4/1988 | Riederer | 128/653.3 |
| 4,767,991 | 8/1988 | Rzedzian | 128/653.2 |
| 4,968,935 | 11/1990 | Ehman et al. | 324/306 |
| 5,051,903 | 9/1991 | Pelc et al. | 324/309 |
| 5,233,302 | 8/1993 | Xiang et al. | 324/309 |
| 5,273,040 | 12/1993 | Apicella et al. | 128/653.2 |

FOREIGN PATENT DOCUMENTS

| | | |
|---|---|---|
| 0269147A2 | 6/1988 | European Pat. Off. |
| 471501A3 | 2/1992 | European Pat. Off. |
| 488496A3 | 6/1992 | European Pat. Off. |
| 0512798A1 | 11/1992 | European Pat. Off. |
| 3918625A1 | 12/1989 | Fed. Rep. of Germany |

OTHER PUBLICATIONS

"Fast Angiography Using Selective Inversion Recovery", Wang, et al., Magnetic Resonance in Medicine, 23, 109–121 (1992).

"MR Fourier Transform Arteriography Using Spectral Decomposition", Cho, et al. Magnetic Resonance in Medicine, 16, 226–237 (1990).

(List continued on next page.)

*Primary Examiner*—K. M. Pfaffle
*Attorney, Agent, or Firm*—Fay, Sharpe, Beall, Fagan, Minnich & McKee

[57] ABSTRACT

A patient's cardiac cycle is monitored (34) for a characteristic point (54) of the cardiac cycle. Following or in response to the characteristic point, a series of field echo sequences (FIG. 3) are applied to generate magnetic resonance echoes (50a, 50b, 50c, etc.) at about 10 millisecond intervals (TR = 10 ms) following the characteristic point. The echoes are phase encoded (44) such that echoes phase encoded in a lowest frequency or central most segment (I) of k-space are generated at regular intervals. Between temporal consecutive segment (I) echoes, echoes with higher frequency phase encoding from segments (II) and (III) (FIG. 4), segments (II–IV) (FIGS. 5A, 5B), etc. are generated. The views are sorted (60) into data sets (62a, 62b, 62c, etc.) such that the central most views are sent to only a single data set and at least some of the higher frequency views are conveyed to two data sets, i.e., the high frequency views are shared or commonly used by two data sets. Each data set is reconstructed (64) into a corresponding frame image representation (66). In this manner, the central most views which carry the most information are unique to each image, but higher frequency views are shared by two temporally adjacent images. The images are displayed sequentially or in another selected order on a video monitor (76).

10 Claims, 6 Drawing Sheets

OTHER PUBLICATIONS

"Cineangiography of the Heart in a Single Breath Hold with a Segmented TurboFLASH Sequence", Aktinson, et al. Radiology 178: 357–360; RSNA 1991.

"A Flow Velocity Zeugmatographic Interlace For NMR Imaging in Humans", Moran, Magnetic Resonance Imaging vol. 1., pp. 197–203 (1982).

"Measurement of Flow with NMR Imaging Using a Gradient Pulse and Phase Difference Technique", Bryant, et al. Journal of Computer Assisted Tomography, 8(4):588–593; Aug. 1984.

"Blood Flow: Magnetic Resonance Imaging", Bradley, et al. Radiology 1985 154:443–450.

Magnetic Resonance of the Cardiovascular System, Edited by Richard Underwood and David Firmin, Oxford Blackwell Scientific Publications, 1991, pp. 116–117.

"Shared Data Dual Echo in Fast Spin Echo Imaging", Hinks, et al. SMRM Book of Abstracts, p. 1011 (1991).

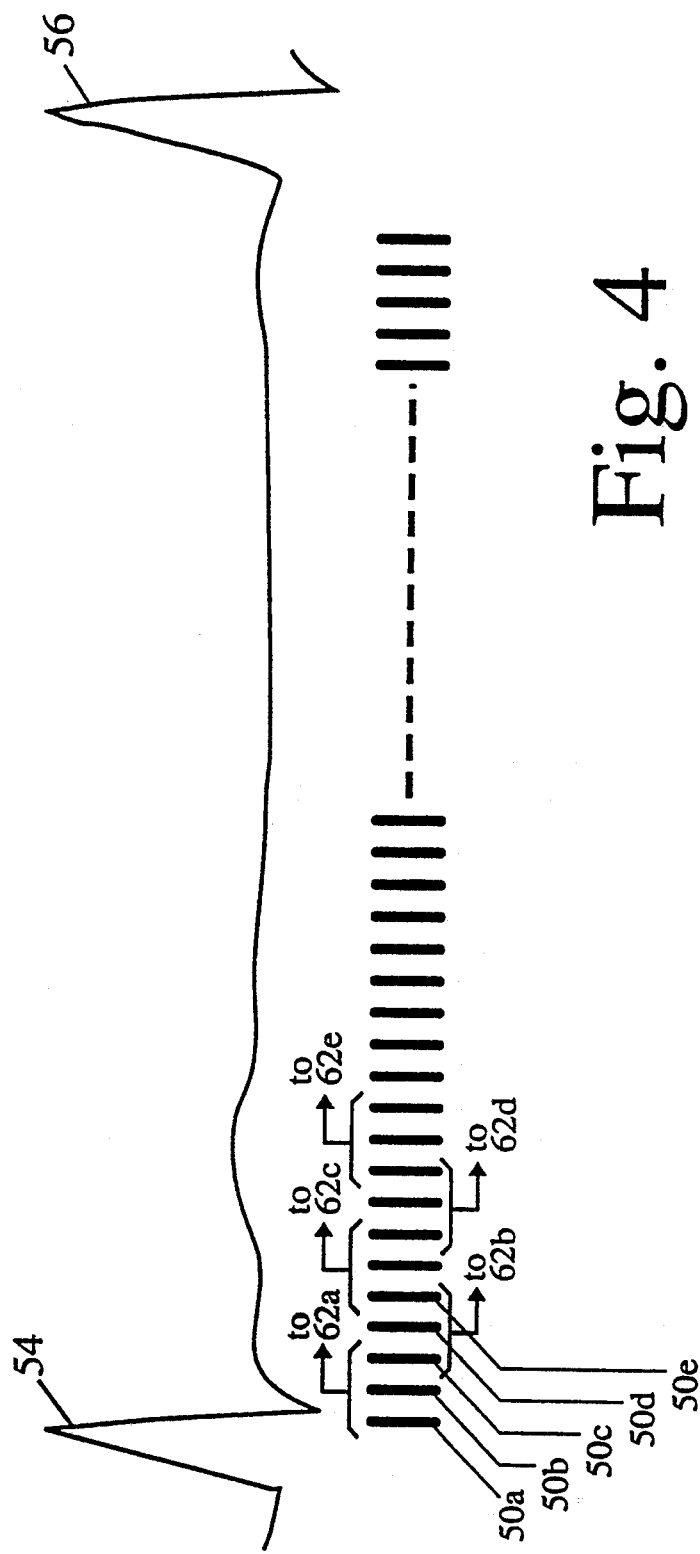

SHARED EXCITATION PHASE ENCODE GROUPING FOR IMPROVED THROUGHPUT CARDIAC GATED MRI CINE IMAGING

This invention is a continuation-in-part of U.S. application 07/874,807 filed Apr. 28, 1992 and U.S. application Ser. No. 07/859,153 filed Mar. 27, 1992 which, in turn, is a continuation-in-part of U.S. application Ser. No. 07/791,855, filed Nov. 14, 1991.

BACKGROUND OF THE INVENTION

The present invention relates to the art of magnetic resonance cine imaging. It finds particular application in conjunction with cine imaging and will be described with particular reference thereto. It is to be appreciated, however, that the invention will also find application in conjunction with angiography, circulatory, cardiac quantitative flow, and other examinations in which flowing fluid or moving tissue is imaged.

Cine images have commonly been acquired using field echoes. Field echoes permit a rapid, e.g. 5–10 msec, repetition rate. In cardiac imaging, about 64 to 100 sequence repetitions can be made in a typical 600 to 1000 msec. cardiac cycle. If the view from each sequence repetition in a common cardiac cycle is allocated to a successive frame, then the cine sequence produces about 64 to 100 frames per cardiac cycle with a resolution of about 10 msec.

Optimal cardiac gated cine images are achieved if all the views are collected within a single breath hold. Collecting all the views within a single breath hold eliminates the motion artifacts attributable to respiratory motion. A single breath hold is typically 16–20 heartbeats. Acquiring only one view per frame image in each cardiac cycle of a single breath hold would limit each frame image to 16–20 views. To increase the number of views per frame, data acquisition could be continued for several breath holds. However, the heart and surrounding tissue move with each respiratory cycle and typically do not return accurately to the same position in subsequent breath holds.

In one technique described in "Cineangiography of the Heart in a Single Breath Hold with a Segmented TurboFLASH Sequence", Radiology, Vol. 178, pp. 357–360, Atkinson and Edelman (RSNA, 1991), 128 lines or views of k-space were grouped into 8 segments of 16 views each. The resultant magnetic resonance echoes of each cardiac cycle were grouped into 16 groups of 8 views each. The number of groups were dependent on the patient's heart rate. The 8 views within each group of 16–20 consecutive heart beats were differently phase encoded and processed as 128 views (16×8) of the same frame image. In this manner, multi-frame images of the cardiac cycle, each with 128 views per image, were generated. More specifically, in the first heart beat, views or lines 1, 17, 33, etc. were collected; in the second heart beat, lines 2, 18, 34, etc. were collected; and so forth. The raw data from these sets was combined or interleaved to form the 128 view data set for reconstruction into each of the multiple frames.

One of the drawbacks of the Atkinson and Edelman segmentation of k-space was that the resultant frames suffered from blurring. The present inventor has recognized that this blurring is attributable to the acquisition of the central views, the views with the most signal power and image information, at different times in subsequent cardiac cycles. In the above-illustrated 8 segment, 16 heart beat sequence, the central views in each group alternated between two different time displaced points in the cardiac cycle.

A fast spin echo imaging technique which acquires data over a wide range of echo times is described in "Shared Data Dual Echo in Fast Spin Echo Imaging" of R. Scott Hinks and Steve Einstein, SMRM Book of Abstracts, page 1011, (1991). Images were acquired corresponding to multiple effective echo times such that each had different properties, e.g. a different $T_2$ weighting. In the Hinks and Einstein technique, each excitation was followed by a plurality of echoes. The central low frequency views were taken in the early echoes and the higher frequency views were taken in the later echoes. To expedite collection, the central, low frequency views, e.g., the central 32 views of a 256 view study were collected twice. The remaining, higher frequency views were each collected once and shared with two lower frequency groups. This produces a significant difference in the $T_2$ weighting between high and low frequency views and a low signal to noise ratio for the high frequency views as compared to a normal spin echo scan.

In parent application 07/874,807, groups of sequential excitations, e.g., 3 excitations in a row, produce 3 echoes in a row which are all used to produce views of a common image. The central most, lowest frequency views are in the center of the group and the higher frequency views are at the beginning and end of the group. By grouping three consecutive echoes into each image, images with an effective temporal resolution of about 30 msec. are achieved with one third as many repetitions as when each echo is processed as a view of a different time displaced frame image. Similar results are achieved for groupings of different sizes.

The present invention provides a new and improved field echo cine technique in which the resultant cine images have more views per frame with better temporal resolution.

SUMMARY OF THE INVENTION

In accordance with the present invention, a cardiac gated series of field echoes is divided into groups. The higher frequency echoes are shared by contiguous groups.

In accordance with a more limited aspect of the present invention, the views within each group are arranged such that the central most or lowest frequency phase encoded views are generated at the same, generally central location within each group in each subsequent cardiac cycle. Higher frequency views are generated before and after each central most view. The higher frequency views are each grouped with both of the two most closely adjacent central views and used in the generation of the corresponding two, time displaced frame images.

In accordance with a more limited aspect of the present invention, the positive half of k-space is divided into n segments of y/2 views each, where y equals the total number of views divided by the group size n. The first and last views of each group are taken from the highest frequency and next highest frequency segments of k-space. At least the highest and next highest frequency segments of k-space are shared each between its two temporally most contiguous frame images.

One advantage of the present invention is that it enables more images to be collected per cardiac cycle.

Another advantage of the present invention is that it reduces the phase encode gradient energy. Fewer of the higher frequency, higher energy phase encoding views are generated.

Another advantage of the present invention is that it provides dynamic cine imaging in which a high frequency encoded echo is shared between two images.

Still further advantages of the present invention will become apparent to those of ordinary skill in the art upon a reading and understanding of the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 4 depicts a heartbeat of a cardiac gated cine acquisition in relative time sequence with views grouped in three's in accordance with a preferred embodiment of the present invention;

DETAILED DESCRIPTION OF THE PREFERRED EMBODIMENTS

Figure 1:
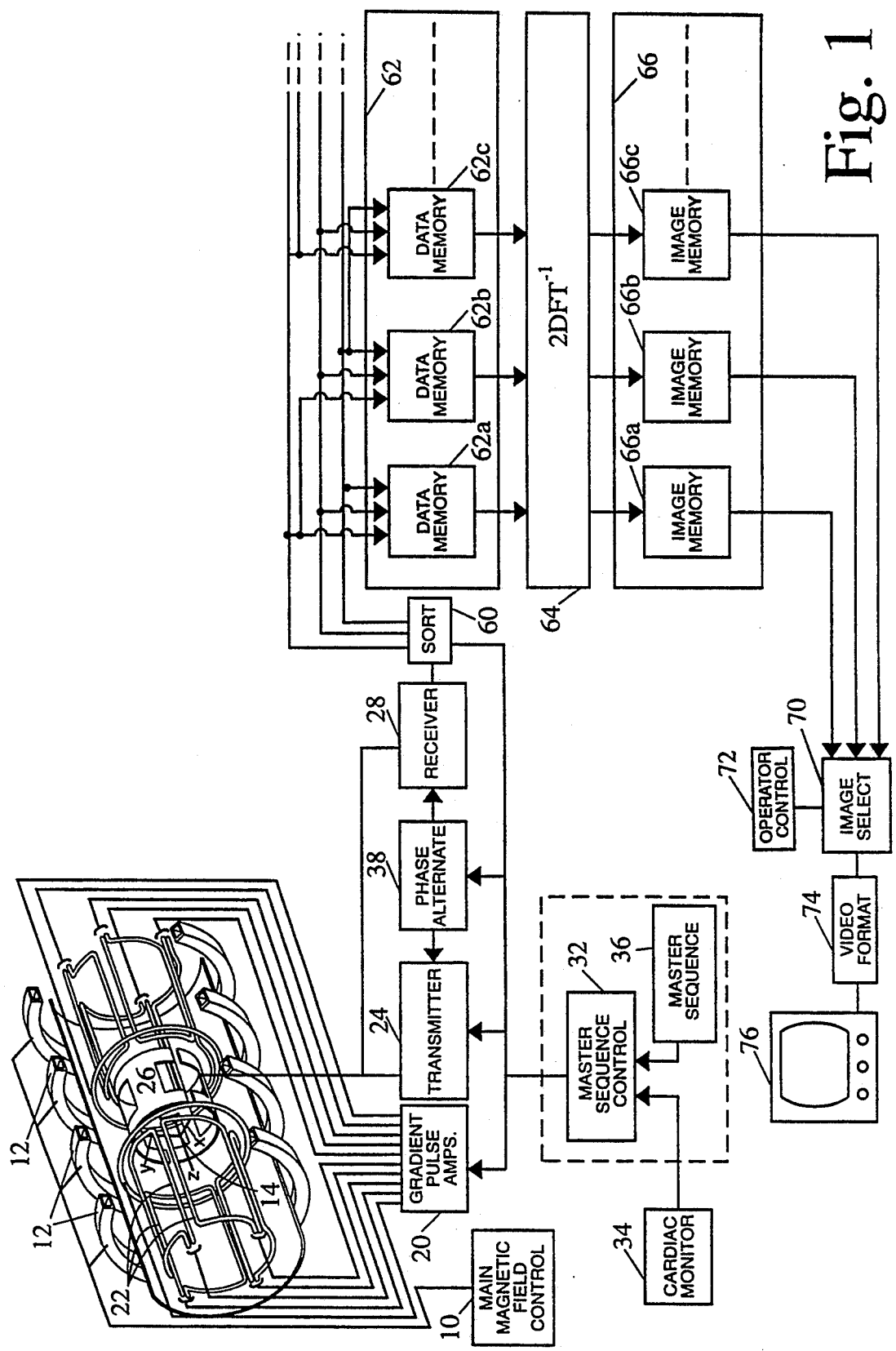
FIG. 1 is a diagrammatic illustration of a magnetic resonance imaging system in accordance with the present invention.

With reference to FIG. 1, a main magnetic field control means 10 controls superconducting or resistive magnets 12 such that a substantially uniform main magnetic field is created longitudinally along a z-axis through an examination region 14. A magnetic resonance echo generating means applies sequences of RF and magnetic field pulses to cause magnetic resonance echoes, preferably field or gradient echoes, to be generated. More specifically, gradient pulse amplifiers 20 apply current pulses to gradient coils 22 to create gradient magnetic fields along orthogonal x, y, and z-axes of the examination region. A radio frequency transmitter 24 transmits RF pulses to an RF coil 26 to transmit RF pulses into the examination to excite magnetic resonance and manipulate excited magnetic resonance. A radio frequency receiver 28 receives magnetic resonance signals emanating from the examination region that are picked up by the RF coil 26 or by surface coils (not shown).

A sequence control means 30 controls the gradient pulse amplifiers 20 and the transmitter 24 to generate a series of field or gradient echo imaging sequences. More specifically to the preferred embodiment, a master sequence control 32 is gated by a cardiac monitor 34 to start a series of field echo sequences. The master sequence control means 32 implements one of a plurality of preselected sequences retrieved from a sequence memory 36. For example, the master control can retrieve and carry out motion sensitive and reference field echo imaging sequences in which the gradients along one of the axes are time or amplitude shifted relative to the other, such as shown for example, in U.S. Pat. No. 4,689,560 of Nayler and Pattany. Preferably, a polarity alternating means 38 causes 0°–180° cycling of the RF. In the preferred embodiment, the phase alternating means causes the phase of the radio frequency excitation pulse and the receiver 28, preferably a digital receiver, to be reversed in alternate views.

Figure 2:
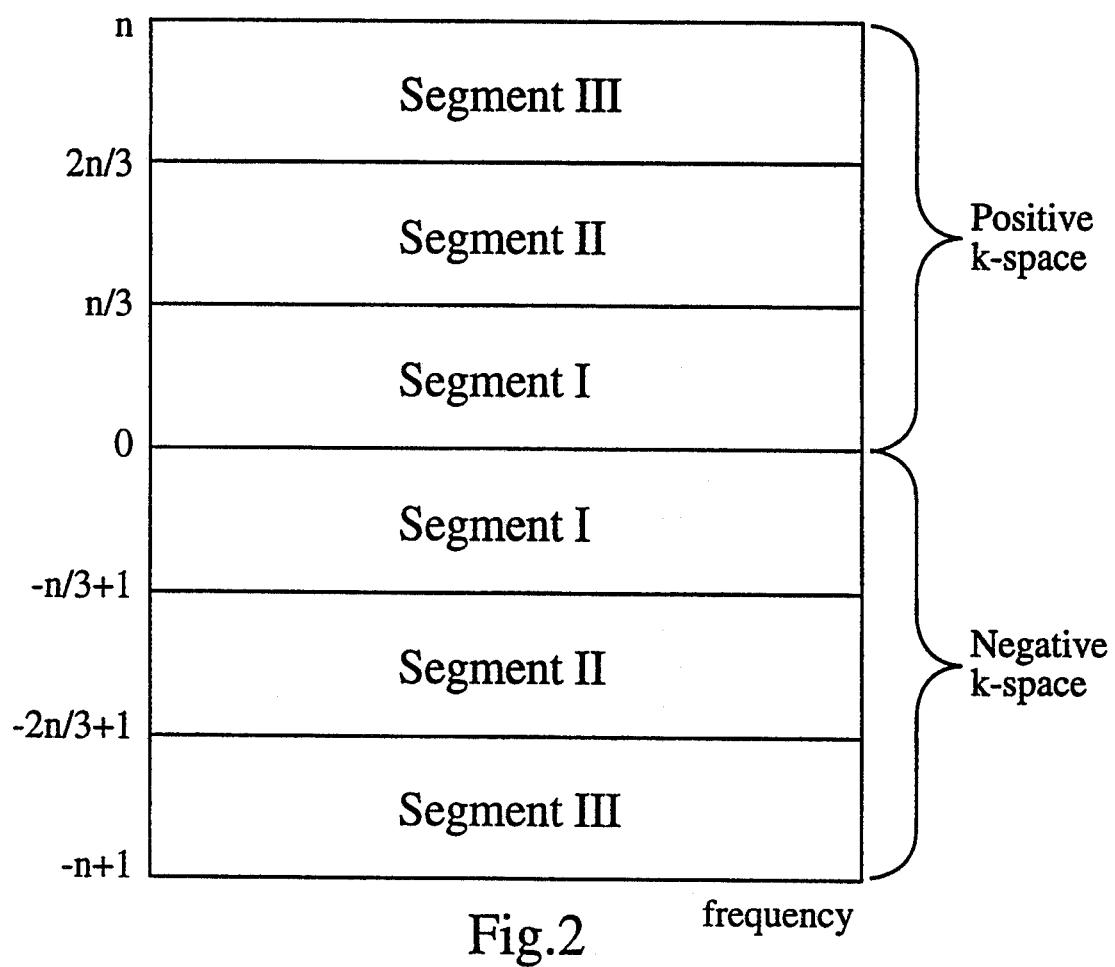
FIG. 2 illustrates a preferred segmentation of k-space.

With reference to FIG. 2, each magnetic resonance echo signal received by the receiver 28 corresponds to one view or line of data of one or more frames of the cine image sequence. Each image is reconstructed from 2n of views, e.g. 252 differently frequency encoded digital views. Each view is phase encoded with one of the 2n phase encodings. To generate full set of views for reconstruction, 2n phase encoded views of data lines are generated. Conventionally, a central view has zero phase encoding. Views to one side of the central view are phase encoded in progressive steps with more phase encoding in a positive sense. Views to the other side are phase encoded in progressive steps of the size but in a negative sense.

Figure 3:
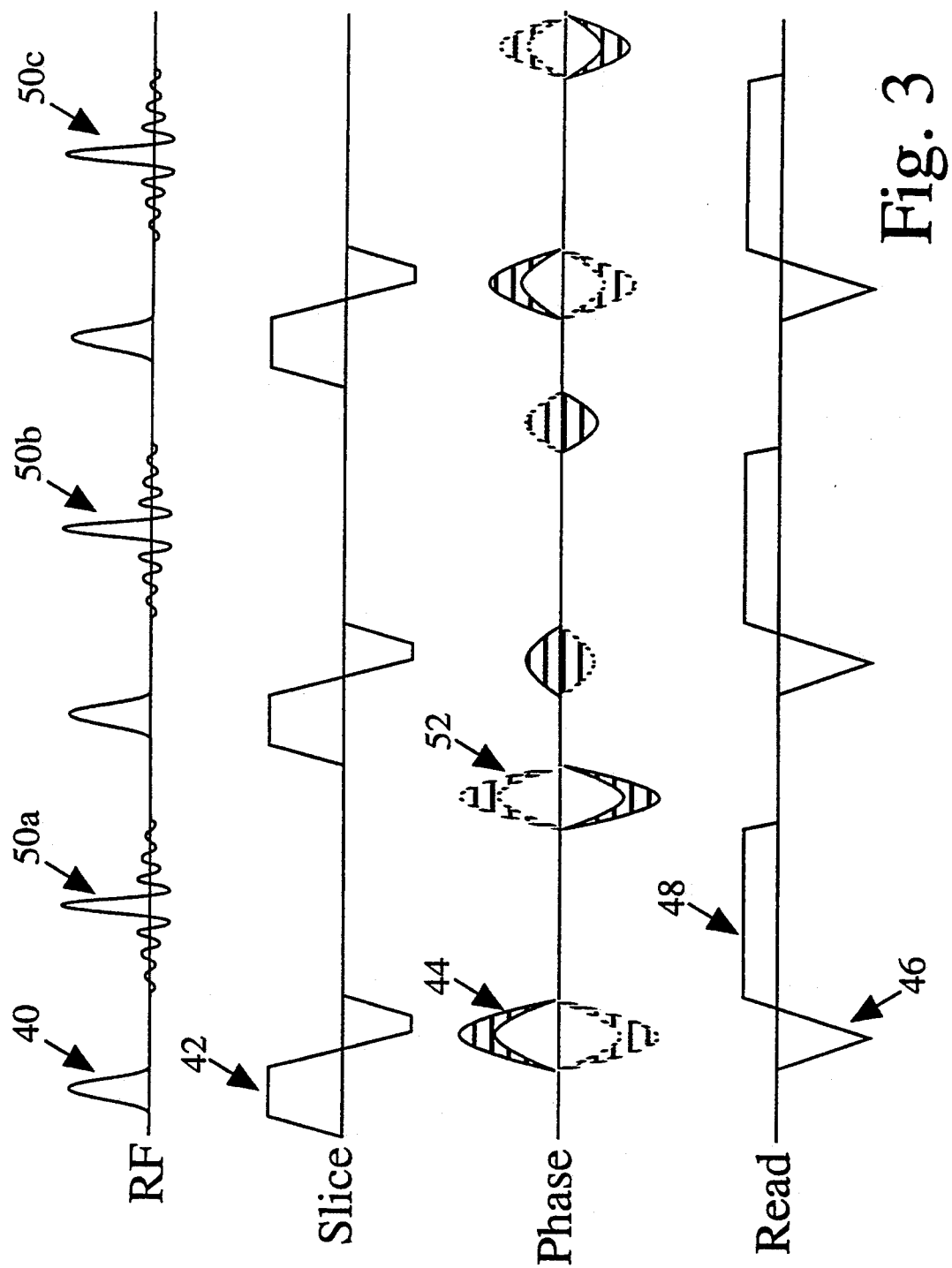
FIG. 3 illustrates an exemplary shared excitation phase encode gradient field echo magnetic resonance sequence.

With reference to FIG. 3, the field echo resonance sequence excites resonance in a selected region, by application of an RF pulse 40, e.g. with a 30° tip angle, and a slice select gradient 42. A phase encoding gradient 44 is applied with a selected one of the 2n phase encoding steps concurrently with a read gradient 46 to phase encode the resultant resonance. The read gradient is reversed to an opposite polarity read gradient 48. A field echo 50 is read during application of the read gradient 48. An unwind phase encoding gradient 59 is applied to remove the phase encoding prior to application of the RF pulse of the next repetition. This sequence is repeated with a repeat time (TR) of about 10 milliseconds.

With reference to FIG. 4, an R-wave 54 of a patient's cardiac cycle is detected by the cardiac monitor 34 which causes the sequence control 32 to initiate the field echo sequence of FIG. 3 which causes the series of echoes 50 during the following cardiac cycle at about 10 millisecond intervals. Typically, 61 repetitions of the gradient echo 50 are generated in the interval before a subsequent R-wave 56.

Returning again to FIG. 1, a sorting means 60 sorts the views into a series of data matrices or memories 62. Each data memory 62a, 62b, etc. receives the data corresponding to one of a plurality of time displaced frame images. Analogously as illustrated in FIG. 2, each magnetic resonance signal produces one view or horizontal data line which is encoded by frequency along its length. Each view is loaded into the data line of the temporally corresponding memory matrix 62a, 62b, etc. in the row corresponding to its phase encoding. Within each heart beat, a plurality of views are collected for each data memory matrix. More specifically, a plurality M of adjacent views from temporally contiguous echoes are each encoded with different phase encodings for one of the frame images. By collecting M views for each image in each cardiac cycle, only 1/Mth as many cardiac cycles are required to collect a full set of views. However, it should be noted that with the present invention, collecting M views of each image per cardiac cycle does not reduce the number of images generated per cardiac cycle to 1/Mth of the number of images that would be generated if only one view per image were collected in each cardiac cycle.

After each of the data memories 62 are filled, the reconstruction means 64 reconstructs the data in each of data memories 62 into a frame image representation which is stored in a corresponding one of a plurality of image memories 66. Preferably, the reconstruction is carried out using an inverse two-dimensional Fourier transform. An image selecting means 70 is controlled by an operator control panel 72 or the like to select one or more frame images for display. A video formatting means 74 adjusts the format of each selected image into an appropriate format for display on a video monitor 76. Preferably, the operator can control the image selecting means 70 to select each frame image representation from image memories 66a, 66b, 66a, etc. in order at a selectable rate such that the video display illustrates movement of the heart during the cardiac cycle cinetographically and can freeze the image at any point in the cardiac cycle.

With continuing reference to FIGS. 1, 2, and 4, a specific example is set forth in which three views of each data set are collected in each cardiac cycle. The 2n views of k-space are divided into three segments, segment I which is the central most or lowest frequency views, segment II which is the intermediate frequency views, and segment III which is the highest frequency views, i.e. has the largest phase encode gradient applied. The excitations of the first three repetitions of the field echo sequence with one of the views in each of the three segments of k-space. More specifically, the central most one of the first three excitations is encoded from the low frequency segment I of k-space. Those on either side, i.e., the first and third excitations are phase encoded to produce one view from segment II and one view from segment III. The sorting means 60 channels these three views to the appropriate data lines of the first memory data set 62a.

Rather than sending the next three data lines to the second data set memory 62b, the sorting means sends the view from a third repetition 50c to the second data set memory 62b as well. A fourth data line from a fourth repetition 50d is caused by the sequence control means 32 to have one of the phase encodings of the low frequency segment I and a fifth data line from a fifth repetition 50e has one of the phase encodings of k-space segment III. That is, the third excitation and the fifth excitation are phase encoded to produce one view with a phase encoding in group II and the other view with a phase encoding from group III. The views from the third, fourth, and fifth repetitions 50c, 50d and 50e are channeled to the second data memory 62b.

Analogously, the fifth view from the fifth repetition 50e is also sent by the sorting means 60 to a third data set memory 62c along with the two following views. That is, the sequence control means 32 causes the sixth view from a sixth repetition 50f to be phase encoded with one of the phase encode gradients of k-space segment I and causes a seventh view from a seventh repetition 50g of the field echo sequence to be phase encoded with one of the views from segment II. This process is repeated for all of the views collected during the cardiac cycle, i.e.

$$\overline{\text{II} \quad \text{I} \quad \text{III}} \quad \overline{\text{I} \quad \text{II}} \quad \overline{\text{I} \quad \text{III}} \quad \overline{\text{I} \quad \text{II}} \dots$$

In this manner, a data set and corresponding frame image are generated at time intervals spaced about 20 milliseconds. More specifically, the central most or lowest frequency views which carry the most information are generated about every 20 milliseconds from every other repetition. The higher frequency views are generated between centrally phase encoded views and shared with the two most temporally adjacent data sets and images. It will be noted that segments II and III need not be maintained distinct. Rather, the views from segments II and III of k-space can be taken in any order or intermixed, provided that each of the data sets acquires a substantially full set of data. Because the first and last views are not shared, if there are 610 milliseconds between cardiac cycles, 61 views can be generated for reconstruction into 30 frame images. It might be noted that if each group of 3 were maintained distinct as in the parent application, only 20 frame images could be generated from the 60 views.

Figure 5A:
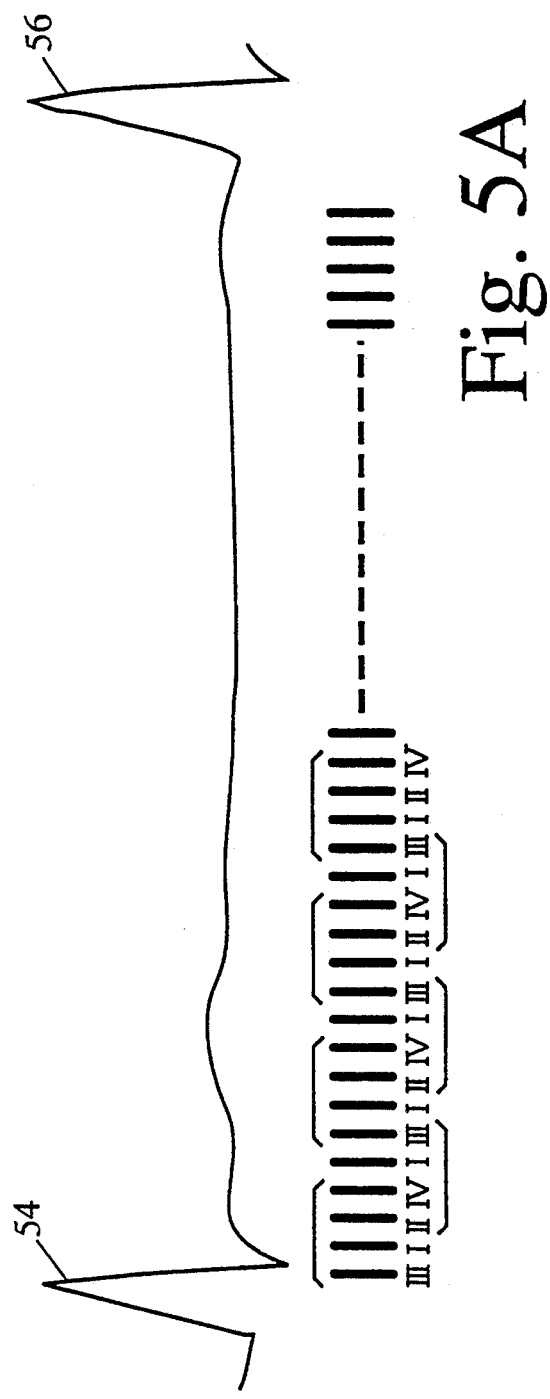
FIGS. 5A and 5B depict a heartbeat of a cardiac gated cine acquisition with k-space divided into four segments.
Figure 5B:
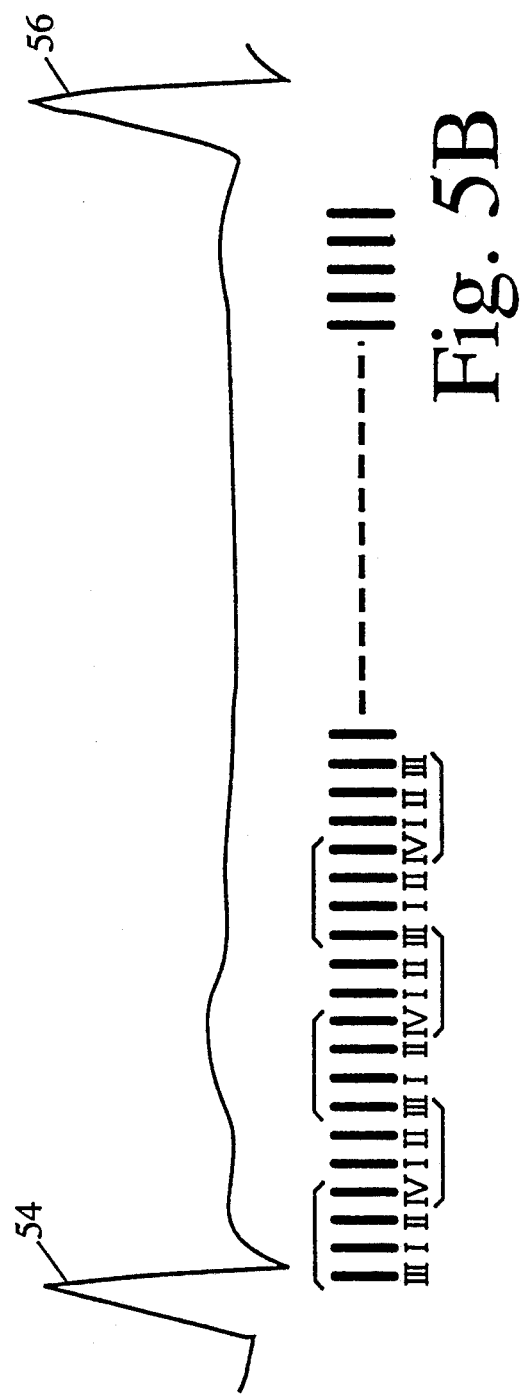

With reference to FIG. 5A and 5B, k-space can be segmented in more than 3 segments, e.g., 4 segments, I, II, III, and IV. With reference to 5A, this data can be grouped such that only the central most data from segment I is unique to each data set and the remainder of the data is shared. With reference to FIG. 5B, alternately, the data from the central most segment I and from the next lowest frequency segment II can be unique to each data set and image and only the two highest frequency segments and IV are shared. Analogously, when k-space is segmented into five segments, I–V, various groupings can be made such as:

$$\overline{\text{IV} \quad \text{II} \quad \text{I} \quad \overline{\text{III} \quad \text{V}} \quad \text{I} \quad \text{IV} \quad \overline{\text{II}} \quad \text{I} \quad \text{III} \quad \text{IV}}$$

$$\overline{\text{IV} \quad \text{II} \quad \text{I} \quad \overline{\text{III} \quad \text{V}} \quad \text{II} \quad \text{I} \quad \overline{\text{IV}} \quad \text{II} \quad \text{I} \quad \text{III} \quad \text{V}}$$

$$\overline{\text{III} \quad \text{II} \quad \text{I} \quad \overline{\text{IV} \quad \text{V}} \quad \text{II} \quad \text{I} \quad \overline{\text{III}} \quad \text{II} \quad \text{I} \quad \text{IV} \quad \text{V}}$$

$$\overline{\text{V} \quad \text{II} \quad \text{I} \quad \overline{\text{III} \quad \text{IV}} \quad \text{II} \quad \text{I} \quad \overline{\text{V}} \quad \text{II} \quad \text{I} \quad \text{III} \quad \text{IV}}$$

$$\overline{\text{V} \quad \text{II} \quad \text{I} \quad \text{III}} \quad \overline{\text{IV} \quad \text{II} \quad \text{I} \quad \text{III}} \quad \overline{\text{V} \quad \text{II} \quad \text{I} \quad \text{III} \quad \text{IV}}$$

Analogous results can be obtained for yet larger segmentations of k-space.

Figure 6:
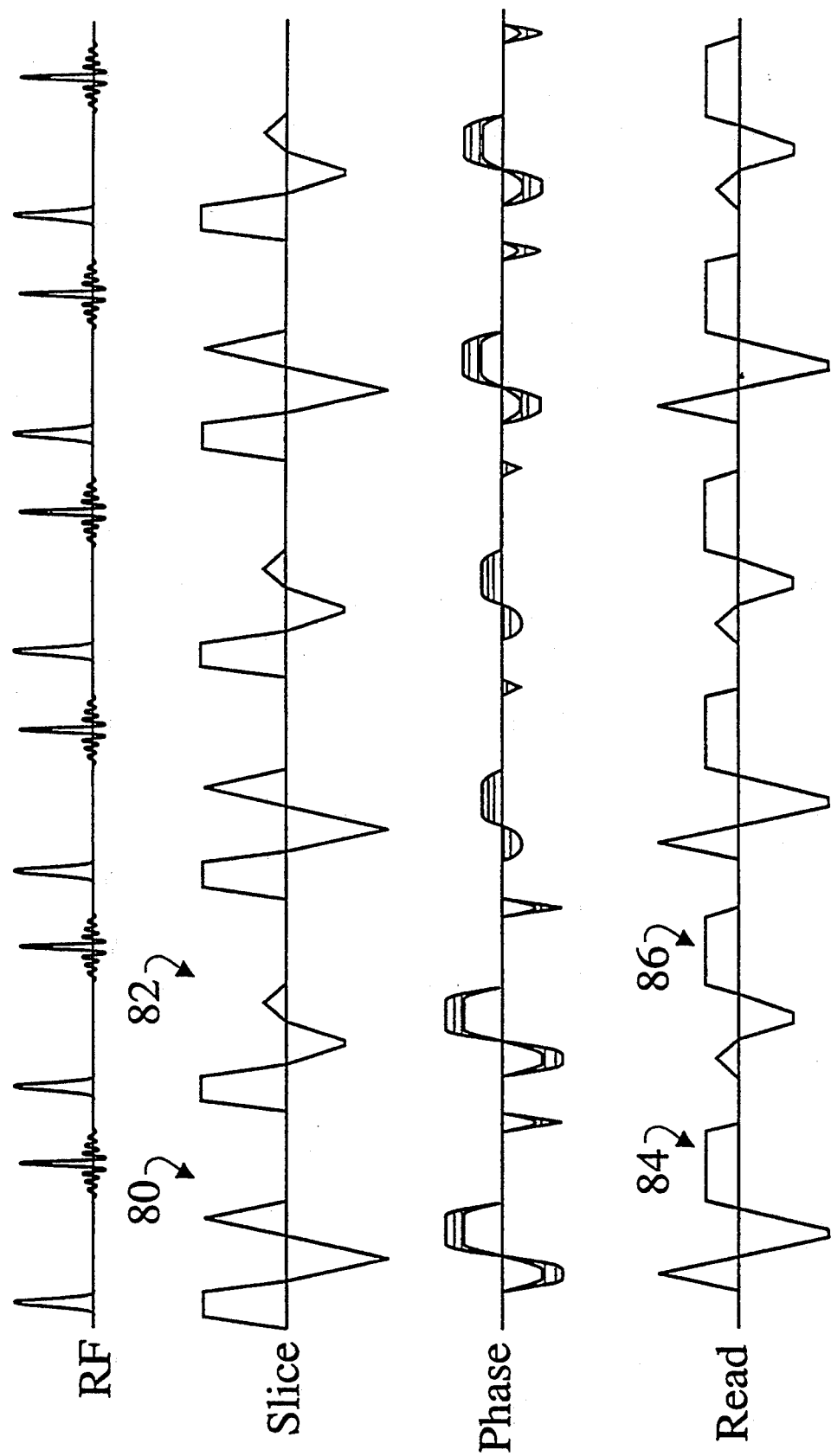
FIG. 6 illustrates a flow encoding shared excitation phase encode gradient field echo magnetic resonance sequence.

In another embodiment, the technique is used to encode flow. More specifically, with reference to FIG. 6, the present technique can be used to encode flow in the slice select direction. A repetition 80 of the slice select gradient is 0th and 1st order moment zeroed. In a next repetition 82, the second and third lobes of the slice select gradient are amplitude scaled to impart velocity encoding. The velocity compensated and velocity sensitized slice select gradients repeat alternately. The read gradient remains unchanged with each repetition. With each subsequent velocity compensated and velocity sensitized slice select gradient pair, the phase encode gradient is changed as set forth in FIGS. 2–5 above. In this manner, the compensated and sensitized pairs are treated as a single unit in reference to the patterns in FIGS. 4 and 5 above.

In a similar fashion, flow can be encoded in the read gradient direction by defining pairs of velocity compensated read gradient repetitions 84 and sensitized read gradient repetitions 86. The slice select gradient remains unchanged with each repetition pair 84, 86. With each subsequent pair, the phase encode gradient is changed as set forth in FIGS. 2–5 above. In this manner, the compensated and sensitized pairs are treated as a single unit in reference to the patterns in FIGS. 4 and 5 above.

Analogously, the motion compensated phase encode gradient repetitions can be velocity sensitized by amplitude scaling of alternate repetitions of the phase encode gradient.

Alternately, the motion sensitized and reference images can be collected in two separate sequences in two breath holds. This maximizes the number of frame images per cardiac cycle, but may create mis-registration between the motion sensitized and reference images. Alternately, the motion sensitized and reference images may be collected in alternate cardiac cycles of the same breath hold. This is advantageous because the reference and motion sensitized scans occur at the same point in the cardiac cycle. Preferably, the reference and motion sensitized views are alternated or interleaved within a single cardiac cycle as explained above and in greater detail in parent application 07/874,807, the disclosure of which is incorporated herein by reference.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A cine magnetic resonance imaging method in which k-space is segmented into at least (i) a central, lowest frequency phase encoding segment and (ii) a higher frequency phase encoding segment, the method comprising:
   (a) monitoring cardiac cycles of a subject in a magnetic resonance imaging region;
   (b) in coordination with each monitored cardiac cycle, generating a series of repetitions of a field echo sequence to cause a corresponding series of magnetic resonance echoes and receiving a corresponding plurality of echo signals, each echo signal corresponding to a view of k-space, the magnetic resonance echoes being phase encoded to produce views of a lowest frequency view component from the central lowest frequency phase encoding segment and two higher frequency view components from the higher frequency phase encoding segment;
   (c) sorting the echo signals such that each lower frequency encoded view component is grouped between immediately preceding the subsequent higher frequency view components and such that each of the two higher frequency view componets are grouped with the two most temporal contiguous lowest frequency view components;
   (d) repeating steps (b) and (c) and stepping phase encoding of the views such that views in the lower frequency view components which are phase encoded with different phase encodings are collected at substantially the same point in time in each of a plurality of monitored cardiac cycles;
   (e) reconstructing a frame image representation from each lowest frequency view component and the immediately preceding and subsequent higher frequency view components.

2. The method as set forth in claim 1 wherein the lowest frequency view components include a single lowest frequency view from the central, lowest frequency phase encoding k-space segment and wherein the higher frequency view components include at least one higher frequency view from the higher frequency phase encoding k-space segment, which said at least one higher frequency view is sorted into two sets.

3. The method as set forth in claim 2 wherein each higher frequency view component includes a single view.

4. The method as set forth in claim 1 wherein the magnetic resonance echoes are phase encoded such that each lowest frequency view component includes a plurality of views from the central lowest frequency phase encoding k-space segment and wherein each higher frequency view component includes at least one view from the higher frequency phase encoding k-space segments.

5. The method as set forth in claim 1 wherein k-space is segmented into at least four segments including the lowest phase encoding segment, the highest frequency phase encoding segment, a first mid-frequency phase encoding segment, and a second mid-frequency phase encoding segment and wherein in step (b), each lowest frequency view component has a view from the lowest frequency phase encoding segment and the first middle frequency phase encoding segment and the higher frequency components have views from the second middle frequency segment and the highest frequency segment.

6. The method as set forth in claim 1 wherein k-space is segmented into at least four segments including the lowest frequency phase encoding segment, a first mid-frequency phase encoding segment, a second mid-frequency phase encoding segment, and a highest frequency phase encoding segment and wherein in step (b) each lowest frequency view component includes a view from the lowest frequency phase encoding segment and each higher frequency view component includes one or more views from the first mid-frequency phase encoding segment, the second mid-frequency phase encoding segment, and the highest frequency phase encoding segment.

7. The method as set forth in claim 1 wherein k-space is segmented into at least five segments and wherein in step (b), each lowest frequency view component is separated from a next temporally adjacent lowest frequency view component by two higher frequency phase encoded views.

8. A cine magnetic resonance imaging method in which k-space is segmented into n segments including a central segment having lowest frequency phase encoded views and a plurality of segments having progressively higher frequency phase encoded views, the method comprising:
   (a) monitoring cardiac cycles of a subject in a magnetic resonance imaging region;
   (b) in coordination with each of a plurality of monitored cardiac cycles, generating a series of magnetic resonance echo sequences each sequence generating a magnetic resonance echo with a phase encoding in one of the n segments, and such that each magnetic resonance echo phase encoded with a phase encoding in the lowest frequency segment has magnetic resonance echoes which are phase encoded with a phase encoding from a higher frequency segment of k-space temporal on either side thereof, and such that magnetic resonance echoes phase encoded with a phase encoding from the lowest frequency segment are generated at regular intervals with magnetic resonance echo phase encodings from higher frequency segments therebetween;

(c) receiving magnetic resonance echo signals corresponding to each of the echoes;

(d) sorting the magnetic resonance echo signals into groups, each group including a magnetic resonance echo signal phase encoded with a phase encoding from the lowest frequency segment and at least two contiguous magnetic resonance echo signals phase encoded with phase encodings from the higher frequency segments, at least one of the magnetic resonance signals from magnetic resonance echoes between temporal adjacent echoes phase encoded with a phase encoding in the lowest frequency segment being sorted into two groups;

(e) repeating steps (b), (c), and (d) with each of the groups at substantially the same time in each of a plurality of monitored cardiac cycles;

(f) reconstructing a magnetic resonance image from each group.

9. A cine magnetic resonance imaging apparatus comprising:

means for monitoring cardiac cycles of a subject in a magnetic resonance imaging region;

means for generating a series of magnetic resonance echoes in coordination with each monitoring cardiac cycle, the magnetic resonance echoes being phase encoded cyclically with low frequency phase encodings and high frequency phase encodings;

means for receiving the magnetic resonance echoes and generating corresponding magnetic resonance signals, the magnetic resonance signals being phase encoded with the corresponding high and low frequency phase encodings;

a plurality of data memory means each for storing a set of data that is reconstructible into a frame image representation, each frame image representation corresponding to a selected temporal point in the cardiac cycle;

means for sorting the magnetic resonance signals such that each of the low frequency phase encoded magnetic resonance signals is stored in a corresponding one of the data memory means and each of the high frequency phase encoded magnetic resonance signals is stored in two data memory means which correspond to the two most temporally contiguous frame image representations;

means for reconstructing a frame image representation from the magnetic resonance signals stored in each of the data memory means, whereby a plurality of temporally displaced frame image representations is generated for each cardiac cycle in which low frequency phase encoded magnetic resonance signals are unique to one of the frame image representations and high frequency phase encoded magnetic resonance signals are shared by temporally contiguous image representations.

10. A cine magnetic resonance imaging apparatus in which k-space is segmented into n segments including a central segment having lowest frequency phase encoded views and a plurality of segments having progressively high frequency phase encoded views, the apparatus comprising:

means for monitoring cardiac cycles of a subject in a magnetic resonance imaging region;

means for generating a series of magnetic resonance sequences in coordination with each of a plurality of the monitored cardiac cycles, each sequence generating a magnetic resonance echo with a phase encoding in one of a plurality of regions of k-space, the magnetic resonance echoes with a phase encoding in the lowest frequency region of k-space being generated at regular, spaced temporal intervals, the magnetic resonance echoes with phase encodings in higher frequency regions of k-space being generated between the echoes in the lowest frequency region of k-space;

receiving means for generating magnetic resonance echo signals corresponding to each of the echoes;

means for reconstructing into frame image representation magnetic resonance signals corresponding to the echoes phase encoded with phase encodings from the lowest frequency region of k-space and the magnetic resonance signals corresponding to echoes phase encoded with phase encodings from higher frequency regions of k-space wherein said higher frequency regions echoes are temporally between two next most contiguous echoes from the lowest frequency regions of k-space.

* * * * *